United States Patent [19]
Celmer et al.

[11] Patent Number: 4,707,493
[45] Date of Patent: Nov. 17, 1987

[54] 19-EPI-DIANEMYCIN AS AN ANTICOCCIDIAL AND ANTIBACTERIAL AGENT

[75] Inventors: Walter D. Celmer, New London; Walter P. Cullen, East Lyme, both of Conn.; Hiroshi Maeda, Chita, Japan; John C. Ruddock, Ash, Near Canterbury, England; Junsuke Tone, Chita, Japan

[73] Assignee: Pfizer Inc.

[21] Appl. No.: 931,587

[22] Filed: Nov. 17, 1986

Related U.S. Application Data

[63] Continuation of Ser. No. 466,468, Feb. 15, 1983, abandoned.

[51] Int. Cl.$^4$ ............................................. C07D 309/10
[52] U.S. Cl. .................................... 514/460; 549/343; 435/118
[58] Field of Search .......................... 549/343; 514/460

[56] References Cited

U.S. PATENT DOCUMENTS

| | | | |
|---|---|---|---|
| 3,577,531 | 5/1971 | Gorman et al. | 424/122 |
| 4,359,583 | 11/1982 | Mizutami et al. | 549/343 |
| 4,366,311 | 12/1982 | Mizutami et al. | 536/123 |
| 4,510,317 | 4/1985 | Liu et al. | 549/343 |
| 4,533,553 | 8/1985 | Celmer et al. | 549/343 |
| 4,625,041 | 11/1986 | Celmer et al. | 549/343 |

FOREIGN PATENT DOCUMENTS 058687 4/1982 Japan .................................. 549/343

OTHER PUBLICATIONS

Westley, Adv. Applied Microbiology 22, 177-223 (1977).

Primary Examiner—Jane T. Fan
Attorney, Agent, or Firm—Peter C. Richardson; Albert E. Frost; Lawrence C. Akers

[57] ABSTRACT

Antibiotic 19-epi-dianemycin, process for its preparation by fermenting a new strain of Streptomyces hygroscopicus, and isolation from the fermentation broth; and its use as an anticoccidial agent and antibacterial agent against gram-positive bacteria.

7 Claims, No Drawings

19-EPI-DIANEMYCIN AS AN ANTICOCCIDIAL AND ANTIBACTERIAL AGENT

This is a continuation of application Ser. No. 466,468, filed on Feb. 15, 1983, now abandoned.

BACKGROUND OF THE INVENTION

This invention relates to a novel polyether antibiotic, to a microbiological process for its production and a process for its recovery. More particularly, it relates to 19-epi-dianemycin, its production by aerobically fermenting a new strain of Streptomyces hygroscopicus, its recovery from fermentation broth, and its use as an anticoccidial agent and antibacterial agent.

Coccidiosis, a common and widespread infection in poultry, is caused by one or more of several species of protozoan parasites of the genus Eimeria. Two types of coccidiosis, cecal and intestinal, are known. The first type is caused by E. tenella and is characterized by severe hemorrhage. The second type is caused by various species of Eimeria such as E. acervulina, E. necatrix, E. maxima, E. hagani, E. mitis, E. praecox and E. brunetti. In turkeys, E. adenoides and E. maleagrimitis are causative organisms of coccidiosis.

The economic effects of coccidiosis are far-reaching and elimination or control of the disease is, therefore, of great importance to the poultry industry.

A wide variety of structural types of compounds have been described as anticoccidials including polyether antibiotics such as monensin [J. Amer. Chem. Soc., 89, 5737 (1967)]; nigericin [Biochem. Biophys. Res. Comm., 33, 29 (1968)]; grisorixin [J. Chem. Soc. Chem. Commun., 1421 (1970)]; dianemycin [J. Antibiotics 22, 161 (1969); U.S. Pat. No. 3,577,531 of May 4, 1971]; salinomycin [J. Antibiotics, 27, 814 (1974)]; X-537A [J. Chem. Soc. Chem. Commun., 967 (1972)]; X-206 [J. Chem. Soc. Chem. Commun., 927 (1971)]; A204A [J. Amer. Chem. Soc., 95, 3399 (1973)]; mutalomycin [J. Antibiotics, 30, 903 (1977)]; ionomycin [J. Amer. Chem. Soc., 101, 3344 (1979)]; K-41B [J. Antibiotics, 32, 169 (1979)]; A-130B and A-130C J. Antibiotics 33, 94 (1980)]; leuseramycin [J. Antibiotics, 33, 137 (1980)]; and A-28695 B [J. Antibiotics, 33, 252 (1980)]. The subject has been reviewed by Westley, "Polyether Antibiotics", Adv. Appl. Microbiol., 22, 177 (1977), and by Shumard et al., Antimicrob. Agents & Chemother. 369–377 (1967).

Swine dysentery, one of the most common swine diseases diagnosed in the United States, is also prevalent in many other countries and annually causes great economic loss. It has recently been discovered that a large spirochete, Treponema hyodysenteriae, is, at the least, a primary source of the infection [Harris, D. L. et al. "Swine Dysentery-1 Inoculation of Pigs with Treponema hyodysenteriae (New Species) and Reproduction of the Disease," Vet. Med/SAC, 67, 61–64 (1972)].

Performance enhancement (increased rate of growth and/or increased efficiency of feed utilization) in ruminants, such as cattle, is another economically desirable objective of veterinary science. Of particular interest is growth promotion achieved by increasing feedutilization efficiency. The mechanism for utilization of the major nutritive portion (carbohydrates) of ruminant feeds is well known. Microorganisms in the rumen of the animals degrade carbohydrates to monosaccharides which are then converted to pyruvates. Pyruvates are metabolized by microbiological processes to form acetates, butyrates or propionates, collectively known as volatile fatty acids (VFA). For a more detailed discussion, see Leng in "Physiology of Digestion and Metabolism in the Ruminant," Phillipson et al., Eds., Oriel Press, Newcastle-upon-Tyne, England, 1970, pp. 408–410.

The relative efficiency of VFA utilization is discussed by McCullough in "Feedstuffs," June 19, 1971, page 19; Eskeland et al. in J. An. Sci. 33, 282 (1971); and Church et al. in "Digestive Physiology and Nutrition of Ruminants," Vol. 2, 1971, pp. 622 and 625. Although acetates and butyrates are utilized, propionates are utilized with greater efficiency. Furthermore, when too little propionate is available, animals may develop ketosis. A beneficial compound, therefore, stimulates animals to produce a higher proportion of propionates from carbohydrates, thereby increasing carbohydrate utilization efficiency and also reducing the incidence of ketosis.

SUMMARY OF THE INVENTION

It has now been found that a new strain of Streptomyces hygroscopicus, isolated from a soil sample collected in Washington, D.C., elaborates a new and valuable antibiotic having anticoccidial properties. This new product was isolated and identified as 19-epi-dianemycin.

DETAILED DESCRIPTION OF THE INVENTION

The antibiotic producing microorganism of this invention was isolated from a soil sample collected in Washington, D.C., U.S.A. It was designated as culture N-483-29. Taxonomic studies of this microorganism were conducted by L. H. Huang who provided the following description. On the basis of his studies he concluded it is a strain of Streptomyces hygroscopicus (Jensen) Waksman and Henrici.

The new culture possesses the narrow hyphae of the Actinomycetales, produces spore chains on the aerial mycelium and an unfragmented substrate mycelium. The results of whole-cell analysis further establish that it belongs to the genus Streptomyces.

The culture N-483-29 is planted from a slant into ATCC #172 broth and grown for three days at 28° C. on a shaker. It is then centrifuged for 20 minutes, washed three times with sterile distilled water and planted on media commonly used for identification of members of the Actinomycetales.

The culture is incubated at 28° C. The results, which may be read at varying times, are most commonly taken at 14 days. The colors are described in common terminology, but exact colors are determined by comparisons with color chips from the Color Harmony Manual, fourth edition. The methods of whole-cell amino acid and sugar analyses are those described in Becker, B. et al., Appl. Microbiol., 12, 421–423, (1964), and in Lechevalier, M. P., J. Lab. Clin. Med., 71, 934–944 (1968).

Identification media used for the characterization of the culture and references for their composition were as follows:

1. Tryptone-Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).

6. Peptone-Yeast Extract Iron Agar—(ISP #6 medium, Difco).

7. Czapek-Sucrose Agar—S. A. Waksman, The Actinomycetes, Vol. 2, medium no. 1, p. 328, 1961.

8. Glucose-Asparagine Agar—Ibid, medium no. 2, p. 328.

9. Bennett's Agar—Ibid, medium no. 30, p. 331.

10. Emerson's Agar—Ibid, medium no. 28, p. 331.

11. Nutrient Agar—Ibid, medium no. 14, p. 330.

12. Gordon and Smith's Tyrosine Agar—R. E. Gordon and M. M. Smith, Jr. Bact. 69, 147-150, 1955.

13. Casein Agar—Ibid.

14. Calcium Malate Agar—S. A. Waksman, Bact. Rev. 21, 1-29, 1957.

15. Gelatin—R. E. Gordon and J. M. Mihm, Jr. Bact. 73, 15-27, 1957.

16. Starch—Ibid.

17. Organic Nitrate Broth—Ibid.

18. Dextrose Nitrate Broth—S. A. Waksman, The Actinomycetes, Vol. 2, medium no. 1, p. 328, 1961, with 3 g dextrose substituted for 30 g sucrose and agar omitted.

19. Potato Carrot Agar—M. P. Lechevalier, Jr. Lab. and Clinical Med. 71, 934-944, 1968 but use only 30 g potatoes, 2.5 g carrots and 20 g agar.

20. 2% Tap Water Agar.

21. Skim Milk—Difco.

22. Cellulose utilization—
  (a) H. L. Jensen, Proc. Linn. Soc. N.S.W. 55, 231-248, 1930.
  (b) M. Levine and H. W. Schoenlein, A Compilation of Culture Media, medium no. 2511, 1930.

23. Carbohydrates—ISP #9 medium, Difco.

24. Temperature Range—ISP #2 medium plus 50 ml coconut milk.

Yeast Extract-Malt Extract Agar—Growth good, tan (near 3ie) with yellowish (2ea) ridges or membranes, moderately raised, wrinkled to membraneous, no aerial mycelium; reverse pale yellowish (2ea) with brown lines (3gc, 3ic); soluble pigment brown (3lc, 3ne).

Oatmeal Agar—Growth moderate, white, yellowish to gray (1 ½ ea, 1 ½ ga, near gray series 3dc, 3fe), thin to slightly raised, smooth, hygroscopic in some areas, aerial mycelium same as surface; reverse colorless, cream to gray (1 ½ ca, near gray series 3dc, 3fe); soluble pigment pale yellowish (1 ½ ca).

Inorganic Salts-Starch Agar—Growth moderate to good, yellowish to gray (1ea, 1 ½ ea, near gray series 3dc, 3fe, 3ih), thin to raised, smooth but wrinkled near the edge, hygroscopic in some areas, aerial mycelium same as surface; reverse pale yellowish to gray (2ea, near gray series 3dc, 3fe); soluble pigment pale yellowish (1 ½ ca).

Glycerol-Asparagine Agar—Growth poor to moderate, colorless to cream (near gray series 1ba), thin, smooth, no aerial mycelium; reverse colorless; no soluble pigment.

Glucose-Asparagine Agar—Growth good, white to cream (2ca), raised, wrinkled, aerial mycelium white; reverse pale yellowish (2ea); soluble pigment pale yellowish (2ca, 2ea).

Czapek-Sucrose Agar—Growth moderate to good, cream (2ca), thin, smooth, with a spreading edge, no aerial mycelium; reverse colorless to cream (2ca); soluble pigment cream (2ca).

Emerson's Agar—Growth good, tan (near 3gc), raised, smooth to slightly wrinkled, no aerial mycelium; reverse same as surface; soluble pigment brown (3lc).

Nutrient Agar—Growth moderate, cream (1 ½ ca, 2ca), slightly raised, smooth or occurring as isolated colonies, no aerial mycelium; reverse pale yellowish (2ca, 2ea); no soluble pigment.

Bennett's Agar—Growth good, cream (2ca), moderately raised, wrinkled to ridged, aerial mycelium none to sparse, white; reverse cream to pale grayish yellow (2ca, 2gc); soluble pigment pale yellowish (2ea).

Gordon and Smith's Tyrosine Agar—Growth poor to moderate, yellowish brown to dark brown (4ec, 4nl, 5nl), thin to slightly raised, smooth, no aerial mycelium; reverse brown to dark brown (5lg, 5ni); soluble pigment dark brown to black (5nl, 5pn).

Calcium Malate Agar—Growth moderate, cream (1 ½ ca), thin to slightly raised, smooth, no aerial mycelium; reverse same as surface; no soluble pigment.

Casein Agar—Growth moderate to good, cream (2ca, 3ca), slightly raised, smooth to slightly wrinkled, no aerial mycelium; reverse cream; soluble pigment pinkish brown (4ia, 4ga).

Gelatin Agar—Growth good, cream (near 2ca), moderately raised, smooth but wrinkled near the edge, no aerial mycelium; reverse same as surface; soluble pigment cream.

Starch Agar—Growth good, cream (near 2ca), moderately raised, wrinkled but may be smooth toward the edge, no aerial mycelium; reverse same as surface; soluble pigment cream.

Potato Carrot Agar—Growth moderate, cream (1 ½ ca), thin, smooth, aerial mycelium sparse, white; reverse colorless to cream; no soluble pigment.

Tap Water Agar—Growth poor, colorless to cream (near gray series 2ba), thin, smooth, mostly submerged, aerial mycelium sparse, white; reverse same as surface; no soluble pigment.

Morphological Properties: The morphological properties were observed on inorganic salts-starch agar after 14 days of incubation: spore mass in Gray color series; spore chains in Section Spirales, slightly open, of small diameter (6–10 $\mu$m long and 3–4.5 $\mu$m wide), 3 to 6 turns per coil, 8 to 30 spores per spore chain; sporophores monopodially branched, sometimes verticillately branched; spores oval to elliptical, occasionally rod-shaped or navicular, 1.2–2.0×0.9–1.2 $\mu$m, warty as revealed by scanning electron microscopy.

Biochemical Properties: Melanin not produced; hydrogen sulfide produced; gelatin liquefied; starch hydrolyzed; nitrate reduced to nitrite in both nitrate broths; poor growth and no decomposition on Jensen's cellulose and Levine and Schoenlein's cellulose; clearing but no coagulation on milk; casein digestion positive; calcium malate digestion positive; tyrosine digestion positive. Carbohydrate utilization: glucose, arabinose, fructose, inositol, mannitol, raffinose, rhamnose, sucrose and xylose all utilized.

| | Temperature Relations: | | |
|---|---|---|---|
| 21° C. | 28° C. | 37° C. | 45° C. |
| Good to excellent growth | Good growth | Moderate growth | No growth |

Whole-Cell Analysis: The cell wall contains LL-diaminopimelic acid but no characteristic sugars.

Culture N-483-29 is characterized by gray spores in mass, spiral spore chains, spores with a warty surface and negative melanin reaction. On some media the aerial mycelium is hygroscopic in some areas. Except for positive utilization of sucrose and raffinose, the isolate fits into the description of the neotype strain of *S. hygroscopicus* published in Int. J. Syst. Bact., 22, 265-394, 1972. The utilization of carbon sources differs among strains according to H. D. Tresner and E. J. Backus, who proposed a broadened concept of the species published in Applied Microbiology, 4, 243-250, 1956. The culture is thus considered as a strain of *Streptomyces hygroscopicus* (Jensen) Waksman and Henrici. It has been deposited in the American Type Culture Collection, Rockville, Md., a recognized depository affording permanence of the deposit and ready accessibility thereto by the public if a patent is granted on this application. This microorganism was given the designation *Streptomyces hygroscopicus* ATCC 39205. Access to the microorganism is available during pendency of this application to one determined by the Commissioner of the U.S. Patent and Trademark Office to be entitled thereto under 37 CFR 1.114 and 35 USC 122. All restrictions on the availability to the public of the microorganism deposited will be irrevocably removed upon granting of the patent.

It is to be understood that the present invention is not limited to use of the aforesaid organism which fully fits the above description, and which is given only for illustrative purposes. It is especially desired and intended to include the use of naturally occurring or artificially induced mutants and/or variants, such as those which can be produced from the described organism, by various means, including x-radiation, ultraviolet radiation, treatment with nitrogen mustards, and the like.

We wish also to include any organism, regardless of its appearance or physiological behavior, that may be developed by means of transformation, transduction, genetic recombination or some other genetical procedure, using a nucleic acid or an equivalent material from the herein described species, whereby it has acquired the ability to produce the elaboration product here described or to carry on the biochemical change here described.

Cultivation of culture *S. hygroscopicus* ATCC 39205 is conducted under submerged aerobic conditions at 21° to 37° C. with agitation in aqueous nutrient media. Typical nutrient media useful for cultivation include a source of assimilable carbon such as sugars, starches and glycerol; a source of organic nitrogen such as casein, enzymatic digest of casein, casamino acids, soybean meal, cotton seed meal, peanut meal, wheat gluten, soy flour, yeast extract, meat meal and fish meal; a source of growth substances such as grain solubles, fish meal, cotton seed meal and yeast extract as well as mineral salts such as sodium chloride and calcium carbonate and trace elements such as iron, magnesium, zinc, cobalt and manganese; and calcium carbonate or phosphates as buffering agents.

If excessive foaming is encountered during fermentation, antifoam agents such as vegetable oils or silicones are generally added to the fermentation medium. Aeration of the medium in tanks for submerged growth is preferably maintained at the rate of about ½ to 2 volumes of sterile free air per volume of fermentation broth per minute forced into the broth through a sparger. Agitation is maintained by means of agitators generally familiar to those skilled in the fermentation art. The rate of agitation depends on the type of agitator employed. A shake flask is usually run at 150 to 200 cycles per minute whereas a fermentor is usually run at 300 to 1700 revolutions per minute. Aseptic conditions must, of course, be maintained through the transfer of the organism and throughout its growth.

Inoculum is prepared by scraping vegetative cells from slants or Roux bottles inoculated with the N-483-29 culture. A solid medium suitable for initial growth on slants and Roux bottles is ATCC medium #172.

| ATCC 172 | Grams/liter |
| --- | --- |
| Glucose | 10 |
| Soluble Starch | 20 |
| Yeast Extract | 5 |
| NZ Amine A | 5 |
| Calcium Carbonate | 1 |
| Distilled Water to 1000 ml; pH to 7.0 with KOH | 20 |
| Add Agar | |

Vegetative cells from slants are used to inoculate either shake flasks or inoculum tanks; or alternately the inoculum tanks are inoculated from shake flasks. In shake flasks growth will generally have reached its maximum in 96 to 120 hours whereas in the inoculum tanks growth will usually be at the most favorable period in 72 to 96 hours. A fermenter is inoculated with vegetative broth from the inoculum flasks or tank under completely aseptic conditions and fermented for a period of 96 to 168 hours. Aeration is maintained in the shake flask by agitation of a shaker or in tanks by forcing sterile air through a sparger at the rate of ½ to 2 volumes of air per volume of broth per minute. The speed of agitation (stirring) depends upon the type of agitator employed as noted above. The temperature is regulated between 24° C. and 36° C.

Upon completion of the fermentation, the antibiotic is recovered by extracting the whole broth with a water-immiscible solvent such as n-butanol, methylisobutyl ketone, ethyl acetate or chloroform at pH from 4.0 to 8.0. Alternatively, the mycelium is separated and extracted with one of the above-enumerated solvents to isolate the antibiotic. The extract is concentrated, the concentrate taken up in heptane and chromatographed on silica gel.

The progress of antibiotic production during fermentation and the bioactivity of the fermentation broth can be monitored by biological assay of the broth employing a sensitive strain of *Staphylococcus aureus* or *Bacillus subtilis*. *S. aureus* ATCC 6538 and *B. subtilis* ATCC 6633 are suitable strains for this purpose. Standard plate assay technique is employed in which the zone of inhibition surrounding a filter paper disc saturated with the broth is used as a measure of antibiotic potency. Also, thin-layer chromatography employing silica gel is a useful tool for analyzing the antibiotic produced in fermentation media and the composition of crude and purified materials extracted from the fermentation broths. The Analtech silica gel GF chromatograms are developed with ethyl acetate/methanol (9:1) or chloroform/methanol (9:1). The antibiotic compound is visualized by spraying with vanillin reagent (3 g vanillin in 75 ml ethanol and 25 ml 85% phosphoric acid) and heating the TLC plate at 80° C. The antibiotic appears as a purple spot. The plate can also be overlayed with agar seeded with either *S. aureus* or *B. subtilis* to which 2,3,4-triphenyl-2H-tetrazolium chloride monohydrate has been added and incubated at 37° C. for 16 hours to visualize the antibiotic (white against a pink background).

Mass spectral data indicated the compound of this invention, as its sodium salt, was isomeric with the sodium salt of dianemycin. Comparison of the $^1$H NMR data of the two salts showed they have the same set of structure units. Two permutations are known to occur in the known polyether antibiotics of the dianemycin class. One involves the position of the methyl group in the A-ring and the other the position of the sugar moiety. The methyl group was determined to be at the 10-position by tracking the sequence of coupled protons from H7 to H11. Since there is only one secondary alcohol function in dianemycin the position of the sugar was determined by establishing that the methine carbon which shows a geminal-$O^2$H isotope shift is bonded to H11.

The differences in the NMR spectra of the sodium salts of dianemycin and of the compound of this invention focus on the C-ring. The sequence of structure units in this ring is unaltered ($^1$H decoupling), but the coupling constants differ, indicating the presence of stereoisomers. The C-ring in dianemycin has the arrangement shown in I below. In the compound of this invention (Na salt in benzene-d$_6$), both H19 and H17 are coupled to the same H18 proton by an

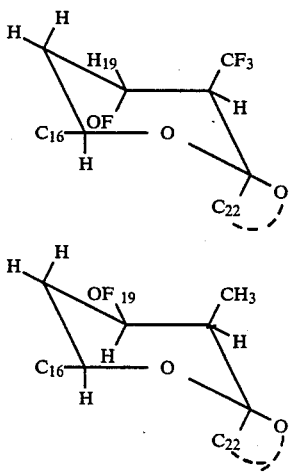

amount ($^3J_{H,H} \sim$ 11 Hz) indicative of a trans-diaxial array. The necessary condition for this is a configurational inversion at either the 17 or 19 position; in the former event, there would also have to be a conformation change to the opposite chair. Since the H19, H20 coupling remains small (<5 Hz), a conformation change would also necessitate inversion at C20; hence; the alternatives are either inversion at C19 with no conformation change, or inversions at C17 and C20 with a conformation change. Since the coupling constants tell us nothing about the configuration at C21, there are a total of four acceptable permutations of configuration in the C-ring. Structure II involves the minimum change, indicating the compound to be the 19-epimer of dianemycin.

In the above partial formulae, "F" represents the F ring, the sugar moiety of dianemycin and of epi-dianemycin.

Antibiotic 19-epi-dianemycin exhibits inhibitory action against a variety of gram-positive microorganisms.

For this test each organism is inoculated in a series of test tubes containing nutrient medium and varying concentrations of 19-epi-dianemycin to determine the minimal concentration of the antibiotic in mcg/ml which inhibits the growth of the organism over a period at 24 hours (MIC).

19-Epi-dianemycin and its cationic salts exhibit excellent activity against coccidial infections in poultry. When incorporated into the diet of chickens at levels of 50 to 200 ppm, these compounds are effective in controlling infections caused by *Eimeria tenella, E. acervulina, E. maxima, E. brunetti* and *E. necatrix*.

Efficacy data for 19-epi-dianemycin and its salts against coccidial infections in chickens was obtained in the following fashion. Groups of 3 to 5 ten-day-old SPF white leghorn cockerel chicks were fed a mash diet containing 19-epi-dianemycin or its sodium and/or potassium salt uniformly dispersed therein. After being on this ration for 24 hours each chick was inoculated per os with oocysts of the particular species of Eimeria being tested. Other groups of 3 to 5 ten-day chicks were fed a similar mash diet free of 19-epi-dianemycin and were not infected with coccidia. These served as normal controls. The results of treatment were evaluated after five days in the case of *E. acervulina*, and six days for all other challenges.

The criteria used to measure anticoccidial activity consisted of lesion scores of 0 to 4 for *E. tenella* after J. E. Lynch, "A New Method for the Primary Evaluation of Anticoccidial Activity", *Am. J. Vet. Res.* 22, 324–326 (1961); and 0 to 3 for the other species based on modification of the scoring system devised by J. Johnson and W. H. Reid, "Anticoccidial Drugs. Lesion Scoring Techniques in Battery and Floor Pen Experiments in Chicks", *Exp. Parasit.* 28, 30–36 (1970). A constant ratio was established by dividing the lesion score of each treated group by the lesion score of the infected control.

The value of animal feeds generally has been determined directly by feeding the animal. British Patent Specification No. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taking place are studied critically and progressively during the consumption of the feed by the microorganisms. An increase in the propionic acid content in the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml added to a 50 ml conical flask containing 400 mg of standard substrate (68% corn starch +17% cellulose +15% extracted soybean meal), 10 ml of a pH 6.8 buffer and the test compounds. The flasks are gassed with oxygen-free nitrogen for about two minutes, and incubated in a shaking water bath at 39° C. for about 16 hours. All tests are conducted in triplicate.

After incubation, 5 ml of the sample is mixed with 1 ml of 25% metaphosphoric acid. After 10 minutes 0.25 ml of formic acid is added and the mixture centrifuged at 1,500 rpm for 10 minutes. Samples are then analyzed by gas-liquid chromatography by the method of D. W. Kellog, *J. Dairy Science* 52, 1690 (1969). Peak heights for acetic, propionic and butyric acids are determined for samples from untreated and treated incubation flasks.

In order to improve feed utilization by ruminants such as cattle and sheep and by monogastric animals such as pigs and rabbits, 19-epi-dianemycin can be incorporated in feed compositions as the free acid, sodium salt, potassium salt or mixtures thereof. Crude forms of 19-epi-dianemycin or dried fermentation broth containing the antibiotic can, of course, be incorporated in feed compositions at the desired potency concentrations.

The following examples more fully illustrate the present invention. They are, however, not to be construed as limiting the scope of the invention.

EXAMPLE 1

Shake flasks were prepared using the following medium:

| CL13M | Grams/liter |
| --- | --- |
| Cerelose | 20.0 |
| Soy Flour | 10.0 |
| Distiller Solubles | 5.0 |
| Sodium Sulfate | 0.5 |
| Cobalt Chloride | 0.002 |
| Calcium Carbonate | 2 |

One hundred ml of medium was distributed into 300 ml shake flasks and sterilized at 120° C. and 15 psi for 30 minutes. After cooling, the medium was inoculated with a vegetable cell suspension from *Streptomyces hygroscopicus* ATCC 39205 grown on ATCC 172 agar medium. The flasks were shaken at 28° C. on a rotary shaker having a displacement of 1½ to 2½ inches and 150 to 200 cycles per minute (CPM) for three to four days. One flask was used to inoculate a five liter fermentation vessel containing three liters of the following media:

| CL13M | Grams/liter |
| --- | --- |
| Cerelose | 20.0 |
| Soy Flour | 10.0 |
| Distiller Solubles | 5.0 |
| Sodium Sulfate | 0.5 |
| Calcium Carbonate | 2.0 |
| Cobalt Chloride | 0.002 |
| Water to 1 liter | |
| pH 6.9-7.0 | |

One milliliter of L61 silicone was added as an antifoaming agent, then the vessels were sealed and sterilized at 120° C. and 15 psi for 45 minutes. The pots were inoculated with one (ca. 3% inoculum) flask, fermented for 96 to 168 hours at 30° C., stirred at 1700 revolutions per minute (RPM) with an air rate of one volume of air per volume of liquid per minute.

When the fermentation was completed (based on an antibiotic disc assay versus *B. subtilis* ATCC 6633) the fermenters were stopped, filtered at the natural pH with the aid of diatomaceous earth. The filtered cake was slurried in methanol, filtered, the solvent concentrated in vacuo, diluted with 2-3 volumes of water, then extracted 2× with ⅛ to ½ volume of a solvent such as methylisobutyl ketone. The solvent layer was separated from the aqueous phase by aspiration or centrifugation, sparkled and concentrated in vacuo to a viscous oil.

Alternatively the antibiotic was isolated by extraction of the whole broth at natural pH with methylisobutyl ketone and concentration of the solvent to a viscous oil. The oil was suspended in heptane and batch treated with silica gel 60. The silica gel cake was eluted with chloroform, chloroform/ethyl acetate and ethyl acetate. After concentration, the ethyl acetate fraction yielded a crude product from which 19-epi-dianemycin crystallized as the mixed sodium/potassium salt.

Thin layer chromatography of the crude product in the following systems, each of which separates a mixture of dianemycin and 19-epi-dianemycin, detected only 19-epi-dianemycin.

| System | Rf Dianemycin | Rf 19-Epi-Dianemycin |
| --- | --- | --- |
| Ethyl acetate | 0.30 | 0.40 |
| Chloroform-Acetone (1:1) | 0.42 | 0.49 |
| Ethyl acetate-Chloroform (2:1) | 0.15 | 0.22 |

Similar results were achieved when one of the following media is substituted for the medium of this example.

| | Grams/liter |
| --- | --- |
| Medium C | |
| Cerelose | 10.0 |
| Corn Starch | 10.0 |
| Soybean Flour | 10.0 |
| Corn Fermentable Solids | 5.0 |
| Sodium Chloride | 5.0 |
| Calcium Carbonate | 1.0 |
| Water to 1 liter | |
| pH 6.9-7.0 | |
| Medium M | |
| Cerelose | 10.0 |
| Starch | 20.0 |
| Yeast Extract | 5.0 |
| Cobalt Chloride | 0.002 |
| NZ Amine A | 5.0 |
| Calcium Carbonate | 1.0 |
| Water to 1 liter | |
| pH 6.9-7.0 | |

EXAMPLE 2

Scale-up of the procedure of Example 1 in large fermenters was carried out by preparing shake flasks containing 0.7 liters of CL13M medium. The shake flask inoculum was fermented for 3 to 5 days at 28° C. and used to inoculate a 1700 gallon (6434.5 liter) fermenter containing 1200 gallons (4542 liters) of CL13M medium. Approximately one liter (0.05%) of inoculum was used in the tank. The fermenter, after fermenting 4 days, was harvested (ca. 1100 gallons, 4164 liters). The whole broth was extracted with 1/5 volume of methylisobutyl ketone at natural pH, separated on a Podbielniack extractor and the solvent concentrated in vacuo to an oil (30.3 liters, 8 gallons).

The oil was further concentrated on a cyclone evaporator to a syrup. After concentration, the oil was suspended in heptane, stirred with silica gel (Merck silica gel 60), then filtered through a bed of silica gel and washed repeatedly with heptane. The antibiotic was eluted stepwise with chloroform, chloroform/ethyl acetate, ethyl acetate and finally 50% acetone in ethyl acetate. The elution was followed by thin layer chromatography and bioassay of the fractions. The active cuts were combined, concentrated and rechromatographed to isolate the antibiotic. During the workup, problems were encountered with the active cuts from the silica gel batch treatment. Passage of the active eluates down granular Darco carbon removed the interferring materials and improved the recovery. Ca. 40 grams of crystalline 19-epi-dianemycin was recovered.

EXAMPLE 3

An approximately 1100 gallon (4164 liter) fermentation of *S. hygroscopicus* ATCC 39205 was prepared according to Example 2. The whole broth was extracted with 1/5 volume of methylisobutyl ketone and the extract concentrated in vacuo to a brown oil (approximately 1 gallon, 3.79 liters). The concentrate was poured into 3 gallons (11.4 liters) of stirring heptane and the resultant slurry was filtered through a bed of diatomaceous earth.

The filtrate was batch treated with 3 kg of Merck column grade silica gel 60 (70–230 mesh). The silica gel was washed with 3 gallons (11.4 liters) each of heptane, chloroform, acetone and methanol. These fractions were examined by thin-layer chromatography and the 19-epi-dianemycin was found to be primarily in the acetone and chloroform fractions.

The acetone fraction (180 g) was chromatographed on an 8×100 cm column packed with Merck column grade silica gel 60 (230–400 mesh) in ethyl acetate. Ethyl acetate was used as the eluting solvent. The flow rate was 70 ml/minute and fractions of approximately 1 liter each were taken. The cuts were examined by thin-layer chromatography on Analtech GF silica gel plates developed in ethyl acetate. The plates were visualized by spraying with vanillin reagent (3 g vanillin in 75 ml ethanol and 25 ml 85% phosphoric acid) and heating to 80° C. 19-Epi-dianemycin appears as a purple spot under these conditions.

The fractions containing 19-epi-dianemycin were combined and evaporated. The concentrate was dissolved in 1 liter of chloroform, washed with 1 liter of acid water (pH 4), then 1 liter of 5% dibasic sodium phosphate buffer (pH 9), dried over anhydrous sodium sulfate, filtered and evaporated. The concentrate was taken up in acetone and a small amount (approximately 10%) of water added, whereupon 19-epi-dianemycin crystallized as the sodium salt. The crystals were collected by filtration and dried in vacuo at room temperature. The yield was 23 g of sodium salt.

The chloroform fraction from the silica gel batch treatment (280 gm) was redissolved in 1 liter of chloroform and passed down a 7×120 cm column packed with granular activated charcoal in chloroform. It was eluted with chloroform at 20 ml/minute and fractions of 300 ml collected. The antibiotic-containing fractions were combined and concentrated. The concentrate was crystallized as the sodium salt form as described above for the acetone fraction. Yield was 14 grams. An additional 10 grams of crude material was obtained as a second crop.

The sodium salt of 19-epi-dianemycin melted at 193°–205° C. Other properties are:
UV $\lambda_{max}$=232nm, $E_{1cm}^{1\%}$ =157
$\alpha_D$= +11.0° (c=1, methanol)

| | Calculated for $C_{47}H_{77}O_{14}Na$: | | |
|---|---|---|---|
| Analysis: | C | H | O + Na (by difference) |
| | 63.49 | 8.73 | 27.78 |
| Found: | 63.10 | 8.86 | 28.04 |

Its infrared absorption spectrum as determined by the KBr disc method showed 47 peaks: 3770, 3690, 3659, 3529, 3487, 3446, 3351, 3186, 2967, 2931, 2874, 2787, 2731, 2701, 2651, 2515, 1716, 1667, 1566, 1462, 1406, 1373, 1333, 1320, 1293, 1271, 1237, 1191, 1164, 1117, 1098, 1065, 1003, 984, 946, 912, 897, 868, 843, 786, 775, 732, 664, 590, 496, 232, 214 cm$^{-1}$.

The free acid was formed by washing a chloroform solution of the sodium salt with acid water (pH 4) then evaporating the chloroform. The compound could not be induced to crystallize, but was obtained as a glass.
UV $\lambda_{max}$=232 nm, $E_{1cm}^{1\%}$=163
$\alpha_D$= +15.6° (c=1, methanol)

| | Calculated for $C_{47}H_{78}O_{14}$: | | |
|---|---|---|---|
| Analysis: | C | H | O (by difference) |
| | 65.10 | 9.06 | 25.84 |
| Found: | 64.45 | 8.94 | 26.61 |

We claim:

1. 19-Epi-dianemycin or a pharmaceutically-acceptable salt thereof.

2. A method for controlling coccidial infections in poultry which comprises administering to said poultry an anticoccidially effective amount of a compound according to claim 1.

3. In a nutrient feed composition for cattle or swine the improvement which comprises said feed containing a compound according to claim 1 in an amount effective to improve feed utilization and promote growth of said cattle or swine.

4. A method for promoting growth of cattle and for increasing the feed utilization efficiency thereof which comprises orally administering to said cattle a growth promoting and feed-utilization efficiency promoting amount of a compound according to claim 1.

5. A method according to claim 3 wherein said compound is administered to said cattle by adding said antibiotic to feed ingested by the cattle.

6. A method for promoting growth of swine and for increasing the feed utilization efficiency thereof which comprises orally administering to said swine a growth promoting and feed-utilization efficiency promoting amount of a compound according to claim 1.

7. A method according to claim 6 wherein said compound is administered to said swine by adding said compound to feed ingested by the swine.

* * * * *

UNITED STATES PATENT AND TRADEMARK OFFICE
CERTIFICATE OF CORRECTION

PATENT NO. : 4,707,493

DATED : November 17, 1987

INVENTOR(S) : Walter D. Celmer et al.

It is certified that error appears in the above-identified patent and that said Letters Patent is hereby corrected as shown below:

Column 12, line 51: "claim 3" should read -- claim 4 --.

Signed and Sealed this

Seventeenth Day of May, 1988

Attest:

DONALD J. QUIGG

Attesting Officer

Commissioner of Patents and Trademarks